United States Patent
Atkinson et al.

(10) Patent No.: US 6,623,931 B2
(45) Date of Patent: *Sep. 23, 2003

(54) DIAGNOSTIC ASSAY FOR ANTIBIOTIC TOLERANCE

(75) Inventors: Robyn M. Atkinson, Memphis, TN (US); Elaine I. Tuomanen, Germantown, TN (US)

(73) Assignee: St. Jude Children's Research Hospital, Memphis, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/054,225

(22) Filed: Nov. 13, 2001

(65) Prior Publication Data
US 2002/0164623 A1 Nov. 7, 2002

(51) Int. Cl.[7] ............... C12Q 1/68; C12P 19/34; C07H 21/04
(52) U.S. Cl. ............ 435/6; 435/91.1; 435/91.2; 536/22.1
(58) Field of Search .............. 435/6, 91.1; 536/22.1

(56) References Cited

FOREIGN PATENT DOCUMENTS

WO    WO 99/57281   * 11/1999 ................ 435/6

OTHER PUBLICATIONS

Novak, R.B., et al., "Emergence of vancomycin tolerance in Streptococcus pneumoniae", Nature 399:590–593 (1999).

Novak, R. et al., "Signal transduction by a death signal peptide: uncovering the mechanism of bacterial Killing by penicillin", Molec Cell 5:49–57 (2000).

McCullers, et al., "Isolation and characertization of vancomycin–tolerant streptococcus pneumoniae from the cerebrospinal fluid of a patient who developed recrudescent meningitis", J. Inf. Disease 181:369–373 (2000).

Normark, et al., "Clinical isolates of streptococcus pneumoniae that exhibit tolerance of vancomycin", CID 32:552–558 (2001).

Abstract # 1776 from the 40th Interscience Conference on antimicrobial Agents and Chemotherapy, Toronto, Canada, Sep., 2000.

Havarstein, et al., "An unmodified heptadecapeptide pheromone induces competence for genetic Transformation in Streptococcus pneumoniae" PNAS, 92: 11140–11144, 1995.

Havarstein, et al., "Identification of the streptococcal competence–pheromone receptor", Mole. Microbiology 21(4):863–869, 1996.

Martin, et al., "Cross–regulation of competence pheromone production and export in the early control Of transformation in Streptococcus pneumoniae" Mol. Microbiology 38(4):867–878, 2000.

* cited by examiner

Primary Examiner—Gary Benzion
Assistant Examiner—Arun K. Chakrabarti
(74) Attorney, Agent, or Firm—J. Scott Elmer

(57) ABSTRACT

Allelic variation in the vex2, pep27 and vncS genes of bacteria responsible for tolerance to antibiotics such as penicillin and vancomycin, is taught. Methods for identifying antibiotic tolerant bacteria and subjects infected with such bacteria, particularly antibiotic tolerant Streptococcus pneumoniae, are provided. Test kits and components useful for performing such methods, particularly including oligonucleotide primers, are also provided.

12 Claims, No Drawings

SEQUENCE LISTING

<160> NUMBER OF SEQ ID NOS: 12

<210> SEQ ID NO 1
<211> LENGTH: 96
<212> TYPE: DNA
<213> ORGANISM: Streptococcus pneumoniae
<220> FEATURE:
<221> NAME/KEY: variation
<222> LOCATION: (41)..(41)
<223> OTHER INFORMATION: residue 41 is a single nucleotide polmorphism
<221> NAME/KEY: variation
<222> LOCATION: (67)..(67)
<223> OTHER INFORMATION: residue 67 is a single nucleotide polmorphism

<400> SEQUENCE: 1
tataacttga tagattatct ttctccgctg gaaaatatcc gattggtcaa caaaaaggca      60
agcaagaata cacttcttga gcttggtttg gatgaa                               96

<210> SEQ ID NO 2
<211> LENGTH: 96
<212> TYPE: DNA
<213> ORGANISM: Streptococcus pneumoniae
<220> FEATURE:
<221> NAME/KEY: variation
<222> LOCATION: (41)..(41)
<223> OTHER INFORMATION: residue 41 is a single nucleotide polymorphism
<221> NAME/KEY: variation
<222> LOCATION: (67)..(67)
<223> OTHER INFORMATION: residue 67 is a single nucleotide polymorphism

<400> SEQUENCE: 2
tataacttga tagattatct ttctccgctg gaaaatatcc aattggtcaa caaaaaggca      60
agcaaggata cacttcttga gcttggtttg gatgaa                               96

<210> SEQ ID NO 3
<211> LENGTH: 84
<212> TYPE: DNA
<213> ORGANISM: Streptococcus pneumoniae
<220> FEATURE:
<221> NAME/KEY: variation
<222> LOCATION: (35)..(35)
<223> OTHER INFORMATION: residue 35 is a single nucleotide polymorphism
<221> NAME/KEY: variation
<222> LOCATION: (46)..(46)
<223> OTHER INFORMATION: residue 46 is a single nucleotide polymorphism

<400> SEQUENCE: 3
atgagaaagg aatttcacaa cgttttatct agtggtcagt tgcttgcaga caaaaggcca      60

```
gcaagagact ataatagaaa atag                                                    84

<210> SEQ ID NO 4
<211> LENGTH: 84
<212> TYPE: DNA
<213> ORGANISM: Streptococcus pneumoniae
<220> FEATURE:
<221> NAME/KEY: variation
<222> LOCATION: (35)..(35)
<223> OTHER INFORMATION: residue 35 is a single nucleotide polymorphism
<221> NAME/KEY: variation
<222> LOCATION: (46)..(46)
<223> OTHER INFORMATION: residue 46 is a single nucleotide polymorphism

<400> SEQUENCE: 4
atgagaaagg aatttcacaa cgttttatct agtgatcagt tgcttacaga caaaaggcca          60
gcaagagact ataatagaaa atag                                                    84

<210> SEQ ID NO 5
<211> LENGTH: 89
<212> TYPE: DNA
<213> ORGANISM: Streptococcus pneumoniae
<220> FEATURE:
<221> NAME/KEY: variation
<222> LOCATION: (79)..(79)
<223> OTHER INFORMATION: residue 79 is a single nucleotide polymorphism

<400> SEQUENCE: 5
tagaacatga aaaattagct tatcgtttcg agatggagga gaatagttta accttcttta          60
tagattttcc aaaagtcgtc caagactag                                              89

<210> SEQ ID NO 6
<211> LENGTH: 89
<212> TYPE: DNA
<213> ORGANISM: Streptococcus pneumoniae
<220> FEATURE:
<221> NAME/KEY: variation
<222> LOCATION: (79)..(79)
<223> OTHER INFORMATION: residue 79 is a single nucleotide polymorphism

<400> SEQUENCE: 6
tagaacatga aaaattagct tatcgtttcg agatggagga gaatagttta accttcttta          60
tagattttcc aaaagtcgcc caagactag                                              89

<210> SEQ ID NO 7
<211> LENGTH: 20
<212> TYPE: DNA
<213> ORGANISM: Streptococcus pneumoniae
<220> FEATURE:
<221> NAME/KEY: primer_bind
<222> LOCATION: (1)..(20)
<223> OTHER INFORMATION: forward PCR primer sequence about 255 bp
      upstream of Vex2 SNP

<400> SEQUENCE: 7
ctgctgaagc agtcctatat                                                         20

<210> SEQ ID NO 8
<211> LENGTH: 20
<212> TYPE: DNA
<213> ORGANISM: Streptococcus pneumoniae
<220> FEATURE:
<221> NAME/KEY: primer_bind
<222> LOCATION: (1)..(20)
<223> OTHER INFORMATION: reverse PCR primer sequence about 160 bp
```

-continued

```
         downstream of Vex2 SNP

<400> SEQUENCE: 8
ttcgacaata tctccagcag                                              20

<210> SEQ ID NO 9
<211> LENGTH: 20
<212> TYPE: DNA
<213> ORGANISM: Streptococcus pneumoniae
<220> FEATURE:
<221> NAME/KEY: primer_bind
<222> LOCATION: (1)..(20)
<223> OTHER INFORMATION: forward PCR primer sequence about 90 bp
         upstream of Pep27 SNP

<400> SEQUENCE: 9
gagctcttgc tggatggtga                                              20

<210> SEQ ID NO 10
<211> LENGTH: 20
<212> TYPE: DNA
<213> ORGANISM: Streptococcus pneumoniae
<220> FEATURE:
<221> NAME/KEY: primer_bind
<222> LOCATION: (1)..(20)
<223> OTHER INFORMATION: reverse PCR primer sequence about 90 bp
         downstream of Pep27 SNP

<400> SEQUENCE: 10
gtctgcaagc aactgaccac                                              20

<210> SEQ ID NO 11
<211> LENGTH: 20
<212> TYPE: DNA
<213> ORGANISM: Streptococcus pneumoniae
<220> FEATURE:
<221> NAME/KEY: primer_bind
<222> LOCATION: (1)..(20)
<223> OTHER INFORMATION: forward PCR primer sequence about 380 bp
         upstream of VncS SNP

<400> SEQUENCE: 11
ccagatgacg caaaatctgg                                              20

<210> SEQ ID NO 12
<211> LENGTH: 20
<212> TYPE: DNA
<213> ORGANISM: Streptococcus pneumoniae
<220> FEATURE:
<221> NAME/KEY: primer_bind
<222> LOCATION: (1)..(20)
<223> OTHER INFORMATION: reverse PCR primer sequence about 30 bp
         downstream of VncS SNP

<400> SEQUENCE: 12
attgattttc ttctaactcc                                              20
```

DIAGNOSTIC ASSAY FOR ANTIBIOTIC TOLERANCE

GOVERNMENT INTEREST

This invention was made in part with U.S. Government support under National Institutes of Health grant no. NIH-AI39482. The U.S. Government may have certain rights in this invention.

FIELD OF THE INVENTION

This invention relates to the field of diagnostics based on DNA sequence information.

BACKGROUND

Antimicrobial resistance to multiple antibiotics is a significant and well described clinical problem; however, a less well-characterized phenomenon, antimicrobial tolerance, has emerged in pathogenic isolates of *Streptococcus pneumoniae* with potentially serious effects on patient outcome. Tolerance describes the ability of bacteria to stop growing in the presence of an antibiotic, while surviving to resume growth once the antibiotic is remove; Incidence of tolerance to vancomycin, the antibiotic of last resort for Gram-positive infections, has increased to 8% in the past few years. Tolerance has also been implicated in-poor patient outcome with pneumococcal meningitis, mortality 30% versus non-tolerant 5% (unpublished data).

In 1997, a locus was identified that is believed to control the activation of the major pneumococcal autolytic enzyme LytA, which is the enzyme whose loss of function is associated with tolerance. Novak R. B. et al, "Emergence of vancomycin tolerance in *Streptococcus pneumoniae*', *Nature* 399:590–593 (1999). The operon, vex/pep27/vncr/s, encodes for a signal peptide, Pep27, that is transported out of the cell via the Vex dedicated transporter. Novak, R. et al., "Signal transduction by a death signal peptide: uncovering the mechanism of bacterial killing by penicillin", *Molec Cell.* 5:49–57 (2000). Pep27 is believed to be a quorum sensing peptide. Novak et al., id. (2000). Once it reaches a critical density in the supernatant, it signals through the two-component regulatory system, VncS and VncR, which subsequently induces activation of LytA. Novak et al., id. (2000).

It has been demonstrated that mutating any one of the genes of the vex/pep27/vncr/s operon prevents proper signaling, resulting in lack of LytA activation and tolerance to penicillin and vancomycin. Novak et al., id. (2000). However, the genetic basis for naturally occurring vancomycin tolerance in the community has not been determined.

SUMMARY OF THE INVENTION

The present invention provides a rapid diagnostic assay to identify strains of bacteria, particularly strains of *Streptococcus pneumoniae*, which are likely to have acquired tolerance to antibiotics. The assay is based on the identification of allelic variations with the vncS, vex2 and pep27 genes that are closely associated with tolerance to penicillin and vancomycin when present.

In one aspect, combinations of vex2 and pep27 alleles which are associated with antibiotic tolerance are taught.

In another aspect, an allele of the vncS gene which is associated with antibiotic tolerance is taught.

Single nucleotide polymorphisms (SNPs) which identify the various vncS, vex2 and pep27 alleles which are relevant to the present invention are taught. According to the present invention, the likely presence of antibiotic tolerant bacterial strains can be identified by determining the presence or absence of these distinctive SNPs in the vncS, vex2 and pep27 genes that are associated with antibiotic tolerance.

Various methods for identifying the SNPs taught herein or and kits providing the components needed to perform such methods are included herein as part of the invention.

DESCRIPTION OF THE SEQUENCE LISTING

SEQ ID No. 1 is a portion of the Type 4 allele of the vex2 gene. The presence of a "G" nucleotide at position 41 and an "A" nucleotide at position 67 identify this as a Type 4 allele.

SEQ ID No. 2 is a portion of the R6 allele of the vex2 gene. The presence of an "A" nucleotide at position 41 and a "G" nucleotide at position 67 identify this as an R6 allele.

SEQ ID No. 3 is a portion of the Type 4 allele of the pep27 gene. The presence of a "G" nucleotide at position 35 and a "G" nucleotide at position 46 identify this as a Type 4 allele.

SEQ ID No. 4 is a portion of the R6 allele of the pep27 gene. The presence of an "A" nucleotide at position 35 and an "A" nucleotide at position 46 identify this as an R6 allele.

SEQ ID No. 5 is a portion of the wildtype allele for the vncS gene. The presence of a "T" nucleotide at position 79 identifies this as a wildtype allele.

SEQ ID No. 6 is a portion of the vancomycin tolerant allele for the vncS gene. The presence of a "C" nucleotide at position 79 identifies this as a vancomycin tolerant allele.

SEQ ID No. 7 is a forward primer for the vex2 gene which hybridizes to a region approx. 255 nucleotides upstream of the SNPs which distinguish the Type 4 allele from the R6 allele.

SEQ ID No. 8 is a reverse primer for the vex2 gene which hybridizes to a region approx. 160 nucleotides downstream of the SNPs which distinguish the Type 4 allele from the R6 allele.

SEQ ID No.9 is a forward primer for the pep27 gene which hybridizes to a region about 90 nucleotides upstream of the SNPs which distinguish the Type 4 allele from the R6 allele.

SEQ ID No. 10 is a reverse primer for the pep27 gene which hybridizes to a region about 90 nucleotides downstream of the SNPs which distinguish the Type 4 allele from the R6 allele.

SEQ ID No. 11 is a forward primer for the vncS gene which hybridizes to a region about 380 nucleotides upstream of the SNP which distinguishes the wildtype allele from the antibiotic tolerant allele.

SEQ ID No. 12 is a reverse primer for the vncS gene which hybridizes to a region about 30 nucleotides downstream of the SNP which distinguishes the wildtype allele from the antibiotic tolerant allele.

DETAILED DESCRIPTION OF THE INVENTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III

[Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Definitions: The terms and phrases used herein to describe and claim the present invention shall have the meanings set forth below.

By "antibiotic tolerance" or "antibiotic tolerant" is meant the ability of bacteria to stop growing in the presence of an antibiotic, while surviving to resume growth once the antibiotic is removed. In contrast to antibiotic resistance, bacterial strains which are antibiotic tolerant cannot be killed by increasing the amount of antibiotic used.

By "oligonucleotide," is meant a molecule comprised of two or more ribonucleotides, preferably more than three. Its exact size will depend upon many factors which, in turn, depend upon the ultimate function and use of the oligonucleotide. The oligonucleotides of the invention are preferably from 10 to 50 nucleotides in length, even more preferably from 20–30 nucleotides in length or from 15–25 nucleotides in length, and may be DNA, RNA or synthetic nucleic acid, and may be chemically or biochemically modified or may contain non-natural or derivatized nucleotide bases, as will be appreciated by those skilled in the art. Also included are synthetic molecules that mimic polynucleotides in their ability to bind to a designated sequence to form a stable hybrid. Such molecules are known in the art and include, for example, peptide nucleic acids (PNAs) in which peptide linkages substitute for phosphate linkages in the backbone of the molecule.

By "primer" is meant an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 10 or more nucleotides, preferably 15–25 nucleotides, although it may contain fewer nucleotides or more nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A labeled oligonucleotide or primer may be utilized in the methods, assays and kits of the present invention. The labeled oligonucleotide may be utilized as a primer in PCR or other method of amplification and may be utilized in analysis, as a reactor or binding partner of the resulting amplified product. In certain methods, where sufficient concentration or sequestration of the subject nucleic acid has occurred, and wherein the oligonucleotide label and methods utilized are appropriately and sufficiently sensitive, the nucleic acid may be directly analyzed, with the presence of, or presence of a particular label indicative of the result and diagnostic of the presence or absence of a particular vex2, pep27 or vncS allele. After the labeled oligonucleotide or primer has had an opportunity to react with sites within the sample, the resulting product may be examined by known techniques, which may vary with the nature of the label attached. The label utilized may be radioactive or non-radioactive, including fluorescent, colorimetric or enzymatic. In addition, the label may be, for instance, a physical or antigenic tag which is characterized by its activity or binding.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently counting procedures may be utilized. In the instance where the label is an enzyme, detection may be accomplished by any of the presently utilized colorimetric, spectrophotometric, fluorospectrophotometric, amperometric or gasometric techniques known in the art.

By "subject" is meant a human or animal which is susceptible to infection by a bacteria which is normally treatable with antibiotics such as penicillin or vancomycin, but which can be antibiotic tolerant if it contains a tolerant form of the vncS allele or a combination of vex2 and pep27 alleles that confers antibiotic tolerance as taught herein.

By "restriction enzyme" is meant a bacterial enzyme which cleaves double-stranded DNA at or near a specific nucleotide sequence referred to as a restriction enzyme recognition site.

Bacterial infections may be treated with a variety of antibiotics. When considering whether to treat an infection with an antibiotic and which antibiotic to use, it is important to know as much as possible about the bacteria causing the infection. In particular, it is very helpful to know in advance if the infection includes a population of bacteria which are tolerant to a particular antibiotic. This knowledge can avoid treatment of infections with antibiotics which will not be effective or treatments that are too short in duration to effectively kill tolerant strains.

The present invention provides methods for rapidly identifying bacteria which are likely to be tolerant to certain antibiotics and which therefore cannot be effectively treated using such antibiotics. These methods are based on the identification of the genetic basis of antibiotic tolerance that has been found in naturally occurring bacterial strains.

The present invention teaches specific allelic variations within the vncS, vex2 and pep27 genes that are closely associated with antibiotic tolerance when present. The variation within the vncS gene that confers tolerance occurs in the region of the vncS gene shown in SEQ ID No. 5. Within this region, the tolerant vncS allele is identified by a change from a thymidine to a cytosine at position 79 of SEQ ID Nos. 5 and 6.

According to the present invention, antibiotic tolerance is also associated with a combination of vex2 and pep27 alleles. Both the vex2 and pep27 genes have alleles designated as "Type 4" and "R6". As taught herein, a specific mismatch between vex2 and pep27 alleles is associated with antibiotic tolerance. Specifically, a bacteria having a combination of a Type 4 vex 2 allele and an R6 pep27 allele is classified as highly likely to be antibiotic tolerant according to the present invention.

The variation that identifies a specific vex2 gene as either a Type 4 or R6 allele is shown in SEQ ID Nos 1 and 2. The Type 4 allele has a guanosine at position 41 and an adenosine at position 67 of SEQ ID No. 1 while the R6 allele has an adenosine and a guanosine at these respective positions (see SEQ ID No. 2).

The variation that identifies a specific pep27 gene as either a Type 4 or R6 allele is shown in SEQ ID Nos. 3 and 4. The Type 4 allele has a guanosine at positions 35 and 46 of SEQ ID No. 3 while the R6 allele has an adenosine at both of these positions (see SEQ ID No. 4).

A bacterial strain which has either (a) the tolerant allele of the vncS gene (SEQ ID No. 6), (b) the specific allelic mismatch between the vex2 and pep27 genes, or (c) both (a) and (b) is identified as likely to be an antibiotic tolerant strain according to the invention.

The allelic variations taught herein as associated with antibiotic tolerance may be identified in the DNA of a selected bacteria using any desired means. Such means includes various conventional techniques for sequencing the critical regions of vex2, pep27 and vncS genes which identify tolerant alleles/allele combinations including pyrosequencing, various conventional polymerase chain reaction (PCR) techniques that can be adapted to detect SNPs such as real time PCR, Invader™ Technology (Third Wave Technologies;Lyamichev et al., *Nature Biotech.* 17:

pep27 alleles associated with antibiotic tolerance. Further, a test kit may be prepared for determining whether a selected bacteria has an allele of the vncS gene associated with antibiotic tolerance. The test kit will include components for the PCR amplification and analysis of critical regions of the vex2, pep27 and/or vncS genes. In one embodiment, the critical region is amplified and then directly sequenced. In an additional embodiment, the critical region is amplified and its sequence at the polymorphic locations identified herein is determined by assessing susceptibility of the PCR product to cleavage with a particular restriction enzyme or a set of restriction enzymes. In a further embodiment, specific primer sets are utilized in amplification of the critical region and the presence or absence of PCR product with the specific primer sets is evaluated to determine the sequence at the polymorphic locations identified herein. Additional reagents for PCR amplification and evaluation may be included in the kit along with directions for use.

In a further aspect, the present invention provides oligonucleotide primers or probes suitable for use in the determination of the vex2, pep27 or vncS genotypes of a selected bacterial strain. Oligonucleotide primers preferably hybridize to a region within 500 nucleotides of the SNP of interest, more preferably within 100 nucleotides of the SNP.

In a particular embodiment, the present invention relates to an isolated oligonucleotide primer having a sequence selected from the group consisting of

```
Vex2
Forward primer: 5' CTGCTGAAGCAGTCCTATAT 3'      ~255bp upstream of SNP (SEQ ID No.7)

Reverse primer: 5' TTCGACAATATCTCCAGCAG 3'      ~160bp downstream of SNP (SEQ ID No.8)

Pep27
Forward primer: 5' GAGCTCTTGCTGGATGGTGA 3'       ~90bp upstream of SNP (SEQ ID No.9)

Reverse primer: 5' GTCTGCAAGCAACTGACCAC 3'       ~90bp downstream of SNP (SEQ ID No.10)

VncS
Forward primer: 5' CCAGATGACGCAAAATCTGG 3'      ~380bp upstream of SNP (SEQ ID No.11)

Reverse primer: 5' ATTGATTTTCTTCTAACTCC 3'       ~30bp downstream of SNP (SEQ ID No.12)
```

292–296 (March 1999), Luminex 11™ technology (Iannone et al., *Cytometry* 39: 131–140 (2000), NanoChip™ Technology (Gilles et al., *Nature Biotech.* 17: 365–370 (April 1999).

As indicated, the polymorphisms which distinguish the alleles in these regions may be identified using polymerase chain reaction (PCR) technology and appropriate primers. Appropriate primers will be designed to amplify regions encompassing the polymorphisms identified herein. Primers may be designed such that, depending on the nucleotide present at the site of the polymorphism, a restriction enzyme recognition site may be created in the amplified fragment. In this case the identity of the nucleotide present at the site of the polymorphism can be determined by testing the amplified fragment for cleavage with the appropriate restriction enzyme.

In a further embodiment of this invention, test kits may be prepared to determine the genotype of a selected bacterial strain with respect to the vex2, pep27 and vncS genes, and thereby determine whether the strain is likely to be antibiotic tolerant.

Accordingly, a test kit may be prepared for determining whether a selected bacteria has a combination of vex2 and The diagnostic and therapeutic utility of the present invention extends to the use of the assays, methods and kits of the present invention in determining whether a subject suffering from a bacterial infection can be effectively treated with antibiotics, particularly penicillin and vancomycin. Samples of the infecting bacteria can be rapidly assayed using the methods of the invention. The information thus obtained from the methods of the present invention can then be used to help predict whether the subject can be successfully treated with a particular antibiotic. For example, if it is determined using the methods of the present invention that a subject is infected with bacteria having a tolerant allele of the vncS gene and/or a mismatch of vex2 and pep27 alleles associated with tolerance as taught herein, it would be predicted that this subject could not be successfully treated with antibiotics such as penicillin or vancomycin. In this case unsuccessful treatment of the subject with these conventional antibiotics could be avoided and alternative therapies could be administered without delay.

The present invention may be better understood by reference to the following non-limiting examples. These examples are presented in order to more fully illustrate the

EXAMPLES

Example 1

Vancomycin Tolerance in Pneumococcal Clinical Isolates

*Streptococcus pneumoniae* is the leading cause of otitis media, meningitis and pneumonia in children and morbidity associated with the bacteria increases as antibiotic resistance increases. Tolerance, a phenomenon distinct from resistance, has also emerged in clinical isolates to contribute to increased morbidity in children. Tolerance describes the ability of bacteria to stop growing and survive in the presence of an antibiotic, yet maintain the ability to grow once the antibiotic is removed. This allows the bacteria to remain at a site of infection to possibly cause relapse of disease and acquire specific resistance markers from the environment since tolerant bacteria are more readily transformable.

This characteristic of the pneumococcus was first described in 1970 in a laboratory mutant lacking the autolytic enzyme LytA. LytA is a murine hydrolase responsible for the degradation of the cell wall during stationary phase and is selectively activated to induce cell wall degradation by certain antibiotics. Therefore, the LytA-mutant was tolerant to penicillin, was deoxycholate (DOC) resistant, and demonstrated slow lysis once in stationary phase. This phenotype became clinically significant in 1985 when 5 of 6 multi-drug resistant isolates of pneumococci we found to be tolerant to β-lactams.

The key to tolerance lies in the mechanisms that control the production and activation of LytA. Four loci have been characterized as indirectly affecting the activation of LytA. Three of these loci inhibit LytA from being produced or placed correctly on the cell surface. Only one of these loci, the vex/pep27/vncR/S operon described in 1999, was implicated as a contributing factor of vancomycin tolerance in a population of pneumococcal clinical isolates. This operon encodes a peptide, Pep27, its putative dedicated ABC transporter, Vex (consisting of Vex 1 and Vex3 as transmembrane proteins and Vex2 containing the ATP-binding domain), and a two-component signaling system, VncR/S. Pep27, a constitutively expressed quorum sensing peptide, is transported into the supernatant via the Vex transporter system. Once the peptide reaches a critical density in the supernatant, it stimulates the receptor of VncS, the histidine kinase portion of a two-component system, to induce autophosphorylation. This signal is received by VncR, the response regulator of the system, to dephosphorylate thereby relieving repression and allowing the transcription of downstream genes to activate LytA and induce lysis of the bacteria. A single point mutation in the signaling component of VncS was found to confer tolerance in a collection of clinical isolates lending this locus to be a candidate for tolerance in the other collections of pneumococcal isolates.

This example describes the results of a study designed to determine the prevalence of vancomycin tolerance in a population of pneumococcal clinical isolates from the nasophraynx of healthy children and to determine the mechanism the strains have employed to confer tolerance.

Prevalence of vancomycin tolerance in clinical isolates. To determine the prevalence of vancomycin tolerance in *Streptococcus pneumoniae* in a population of healthy children, 215 nasopharygeal isolates from Vanderbilt University Hospital were screened for lysis after exposure to 10×MIC (minimum inhibitory concentration) vancomycin (5 ug/ml). 27 of the 215 isolates (12.5%) failed to lyse as evidenced by persistent optical density of the culture above 0.15 after 4 hours (control R6 strain: $OD_{620nm}$ of 0.02 after 2 hours @ 10×MIC of vancomycin). These 27 isolates exhibited behavior similar to the tolerant laboratory mutant Lyt4-4 ($OD_{620nm}$ remained between 0.150 and 0.200 after treatment with vancomycin).

To confirm tolerance, the 27 non-lytic strains were subjected to viability assays. Eight demonstrated <3 log killing after 4 hours of exposure to vancomycin as compared to the R6 strain (5 log kill). This is within ±2 standard deviations (SD) of the killing rate for the tolerant Lyt4-4 strain. The remaining 19 non-lytic isolates were dead after antibiotic exposure indicating they were not actually tolerant.

Characteristics of Tolerant Isolates. The MIC's of the tolerant isolates ranged from 0.1 ug/ml to 0.3 ug/ml vancomycin and all were resistant to penicillin as evidenced by an oxacillin disc sensitivity test. Tolerance was not correlated with serotype. Frequently, tolerant strains were isolated days to weeks after non-tolerant strains in the same child indicating tolerance could arise during carriage in the nasopharynx. Clonal relatedness between the non-tolerant and tolerant strains isolated sequentially from the same child was assessed by pulse-field gel electrophoresis (PFGE) patterns of SmaI digested genomic DNA. Sequential isolates from the same child possessing the same serotype were genetically highly related. Thus, tolerant and non-tolerant strains could be paired for comparison. PFGE indicated a possible serotype switch in one child (Child C), while another child (Child E) was colonized by two separate, yet closely related, tolerant strains. The multiple distinctive PFGE patterns from different children indicates that tolerance has developed in several different genetic backgrounds.

Identification of the Mechanism Contributing to Tolerance. Immunoblotting demonstrated that LytA was present in eluates of surface proteins of all tolerant strains. Furthermore, all tolerant isolates were lysed by 1% deoxycholate—a detergent that specifically activates functional LytA causing lysis of the bacteria. This eliminated mechanisms of tolerance in the clinical strains that arise from lack of enzyme or loss of amidase activity. Attention thus focused on the only reported mechanism where normal amidase is present: mutation of the vncR/S locus, encoding a two-component sensor regulator system. Western blot analysis confirmed the presence of VncS and VncR in the tolerant clinical isolates. DNA sequence analysis in the clinical isolates revealed no mutations in either vncS or vncR. These results indicated a novel mechanism was operative in these 8 clinical isolates.

Pep27 Transport by Vex. In laboratory strains, tolerance has been created by loss of function mutations in the death signal Pep27 or its transporter Vex, the loci contiguous with vncS/R. Tolerance in these cases was attributed to lack of Pep27 or lack of Pep27 export into the supernatant. To assess Pep27 in the supernatant, immunoprecipitations were performed using Pep27 antibody. Results from dot blot analysis of the immunoprecipitation elutions indicated that less Pep27 was present in the supernatant of tolerant strains when compared to R6 and non-tolerant partners. Therefore, extracellular transport of the peptide may be defective in tolerant strains leading to the loss of signal for death through VncS. If so, tolerance should be reversed through the addition of exogenous Pep27 to the culture. To test this, tolerant clinical strains were treated with vancomycin at 10×MIC as before but 0.5 mM synthetic Pep27 was added in conjunction with the antibiotic. The tolerant strains showed a rapid loss of optical density, comparable to R6, and viability was diminished by 4 logs when compared to 2 logs in the absence of peptide. A similar effect was seen with a loss of function mutation in Vex1, the transmembrane component of the transporter.

This evidence points toward a defective transporter, Vex, or peptide, Pep27. Vex, the putative dedicated ABC transporter directly upstream of the pep27/vncS/R in this locus, encodes for a mechanism previously reported to export Pep27 into the supernatant. vex and pep27 were screened for mutations via DNA sequencing in TIGR4, R6, tolerant and non-tolerant strains. Sequence information from pep27 revealed two alleles for this peptide. One allele is represented by the published sequence of TIGR 4, and the other is represented by the R6 reference strain (see SEQ ID Nos. 3 and 4). The single nucleotide polymorphisms or SNP's identified result in 2 amino acid changes. Sequencing of vex1, vex2, and vex3 in Type 4 vs. R6 revealed two alleles for vex2, the ATP binding component of this transport mechanism. These SNP's also result in two amino acid changes within the different isotypes (see SEQ ID Nos. 1 and 2).

DNA sequence analysis of the vex2 and pep27 regions of the tolerant isolates revealed that 5 out of 8 of the tolerant isolates paired a Type4 vex2 allele and an R6 pep27 allele. This specific mismatch was heavily correlated to tolerance (5 out of 8 tolerant vs. 8 out of 33 non-tolerant). This raised the hypothesis that alleles of pep27 and vex2 may form specific pairs without which the export pathway is defective. Specifically if Pep27 is not exported into the supernatant, the quorum-sensing mechanism to activate LytA will not be triggered. The hypothesis predicts that a mismatch of alleles, as occurred in a majority of the tolerant isolates, contributes to tolerance.

Extracellular transport of a substrate by an ATP binding cassette transporter begins with binding of the substrate, in this case Pep27, to the cytoplasmic binding protein, in this case Vex2, to induce conformational changes allowing for transport. In order to assess such an interaction, co-immunoprecipitation was performed. Vex2 was precipitated in conjunction with Pep27 and its antibody. However, the interaction was demonstrated in both tolerant strains and their non-tolerant partners, indicating that binding occurs despite allelic variation. Since binding of substrate to transporter appears normal in tolerance associated with this mismatch, release of the peptide from Vex2 and subsequent transport out of the cell is faulty.

The results described herein indicate that tolerance to vancomycin is an attribute circulating in pneumococci within the community. Our data show that 4% of a population of pneumococci isolated from healthy children were tolerant to vancomycin. The eight clinical isolates had the classic signature of tolerance; slow lysis in antibiotic susceptibility assays and enhanced survivability after antibiotic exposure.

However, a subset of the population, 19 of 215 isolates, that were killed by vancomycin (no growth once the antibiotic was removed) displayed a non-lytic phenotype (little to no lysis observed in the autolysis assay). Tuomanen et al (J Infect Dis. 158:36–43, 1988) first described varying degrees of lysis in the pneumococci including a phenotype with dissociation of lysis and death. The bacteria appear to survive antibiotic treatment by demonstrating slow lysis, yet antibiotic successfully killed the bacteria (as seen by a marked drop in viability after treatment). They conclude that these bacteria could cause an altered course of disease in an individual and created a third class of antibiotic response. Our data supports this classification and show it is still prevalent in the community.

Pulse field gel electrophoresis analysis of the tolerant strains show they are genetically related to non-tolerant strains isolated previously from the nasopharynx of the same child. This indicates that tolerance possibly developed during carriage. PFGE pattern analysis also indicated that tolerance to vancomycin has developed in several different genetic backgrounds and the increased incidence of tolerance is not the result of spread of a single clone.

To date, five mechanisms have been shown to contribute to tolerance in the laboratory: the original loss of LytA mutant and four mutants that affect translation, export or activation of LytA. All tolerant clinical isolates in this series had functional and correctly exported autolytic enzyme, LytA, eliminating three of the mechanisms responsible lack of translation and defective export. The remaining mechanism implicated previously in a collection of tolerant clinical isolates centers on signal transduction and activation of LytA.

Pep27 a putative quorum-sensing peptide that signals the pneumococcus to die is exported from the cell via an ABC-transporter, Vex. Once the peptide reaches a critical density in the supernatant, it signals for lysis through interactions with VncS, the histidine kinase sensor molecule of a two-component regulatory system. VncS then dephosphorylates the response regulator, VncR, of the two-component system relieving repression of genes that activate LytA. Novak et al demonstrated that a loss of VncS or Pep27 induced tolerance in the pneumococcus. Our sequence and immunoblotting data show that these two parts of the system are intact and free of mutations in the current series of strains. However, two alleles for Pep27 and a component of its transporter, Vex2, were discovered. One allele is specific to the reference strain R6 and one specific to the published strain Type 4.

This allelic variation is parallel to that seen with the competence stimulating peptide (CSP) in the pneumococcus. The CSP system is one of several examples in gram-positive bacteria of cell—cell interactions that are controlled by peptides. In this system, competency, the ability of the pneumococcus to take up pieces of DNA from the environment, is controlled through the quorum-sensing actions of the CSP. Once CSP reaches a critical density, it signals through its histidine kinase, ComD, to phosphorylate ComE, the response regulator, and allow for induction of genes involved in competence. CSP is unique in that there are two or possibly three alleles of the peptide involved in the process. The pneumococcus will produce a specific peptide that is exported into the media and that peptide must correctly match one of the two alleles for the histidine kinases (HK) on the surface of the bacteria in order for the induction of competence. Allelic variation creates a level of specificity for the system where a correct match must occur for proper function. It is possible for our system of LytA activation to have a similar level of specificity to ensure proper lysis.

However, variation in our system was localized to the transporter system, Vex. Vex has three components. Vex1 and Vex3 are transmembrane proteins and Vex2 is the ATP-binding/hydrolyzing portion of the transporter hypothesized to physically bind the exported substrate. Sequences reveal that there are two alleles for the Vex2 portion of the transporter. It is contemplated that a direct interaction between Pep27 and Vex2 must occur in order to achieve export of the peptide. Without this correct pairing, Pep27 would not be exported and could not signal death, thereby conferring tolerance. It was seen that most of the tolerant strains carried the Type 4 Vex2 specific allele. Since these same strains carry the R6 Pep27 allele, this mismatch of components is contemplated to lead to tolerance.

The contemplation of a defective transporter mechanism as the cause of tolerance is enhanced by the finding that Pep27 does not make it into the supernatant of tolerant isolates in an amount comparable to strains that lyse appropriately. Also, synthetic Pep27 added exogenously to tolerant strains in conjunction with the addition of vancomycin restored their ability to be killed by this antibiotic.

Specificity harbored by a transporter introduces a new significance to the action of ABC transporter systems. Recently, it was noted that some specificity in the competency system lies within the CSP transporter ComA/B. The transporter in this case is the rate-limiting step controlling the export of the peptide affecting the rate and efficiency of competence. Without functional ComA or with it overexpressed, the degree of competency can be controlled in the pneumococcus. Therefore, Pep27 transport specificity is a novel mechanism but not without foundation.

The study described in this example demonstrates that tolerance is present in the community. Tolerance can arise in several genetic backgrounds but all tolerant clinical strains appear to mutate the same system to create tolerance.

We claim:

1. A method for determining whether a bacteria is likely to be tolerant to at least one antibiotic comprising (a) determining whether said bacteria has a type 4 or R6 allele of the vex2 gene, and (b) determining whether said bacteria has a type 4 or R6 allele of the pep27 gene, wherein said bacteria is determined to be likely to be tolerant if it has a type 4 allele of the vex2 gene and an R6 allele of the pep27.

2. The method of claim 1 wherein said antibiotic is a β lactam.

3. The method of claim 1 wherein said antibiotic is selected from the group consisting of penicillin and vancomycin.

4. The method of claim 1 wherein the step (a) is accomplished by determining the nucleotides present in the vex2 gene of said bacteria at the locations corresponding to nucleotides 41 and 67 of SEQ ID No. 1, and step (b) is accomplished by determining the nucleotides present in the pep27 gene of said bacteria at the locations corresponding to nucleotides 35 and 46 of SEQ ID No. 3.

5. The method of claim 4 wherein steps (a) and (b) are accomplished by sequencing a region of the genomic DNA of said bacteria which includes said locations.

6. The method of claim 4 wherein steps (a) and (b) are accomplished by (i) amplifying a region of the genomic DNA of said bacteria which includes said locations to generate an amplified fragment, and (ii) treating the amplified fragment with a restriction enzyme in its corresponding restriction buffer to determine the identity of the nucleotide present at the selected locations.

7. The method of claim 4 wherein steps (a) and (b) are accomplished by (i) amplifying a region of the genomic DNA of said bacteria which includes said locations, and (ii) hybridizing the amplified region with probes specific for the selected locations wherein hybridization determines the identity of the nucleotide present at the selected locations.

8. The method of claim 1 further comprising determining whether said bacteria has a wildtype or tolerant allele of the vncS gene, wherein said bacteria is also determined to be tolerant if it has the tolerant allele of the vncS gene.

9. A method for determining the vex2 genotype of a selected bacteria comprising determining the identity of the nucleotides located at the positions corresponding to nucleotides 41 and 67 of SEQ ID No. 1 in the genomic DNA of said selected bacteria.

10. The method of claim 9 comprising the steps of:
(a) isolating nucleic acid from the bacteria;

(b) amplifying a region of the vex2 gene which includes the locations corresponding to nucleotides 41 and 67 of SEQ ID No. 1; and (c) determining the identity of the nucleotides located at the positions corresponding to nucleotides 41 and 67 of SEQ ID No. 1.

11. A method for determining the pep27 genotype of a selected bacteria comprising determining the identity of the nucleotides located at the positions corresponding to nucleotides 35 and 46 of SEQ ID No. 3 in the genomic DNA of said selected bacteria.

12. The method of claim 11 comprising the steps of:

(a) isolating nucleic acid from the bacteria;

(b) amplifying a region of the pep27 gene which includes the locations corresponding to nucleotides 35 and 46 of SEQ ID No. 3; and (c) determining the identity of the nucleotides located at the positions corresponding to nucleotides 35 and 46 of SEQ ID No. 3.

* * * * *